(12) United States Patent
Zlotnik et al.

(10) Patent No.: US 7,857,236 B2
(45) Date of Patent: Dec. 28, 2010

(54) APPARATUS FOR DISPENSING AN AROMATIC ODOR NEUTRALIZER

(75) Inventors: Arnold H. Zlotnik, Pittsburgh, PA (US); Raymond Czapko, Pittsburgh, PA (US); Eric R. Colburn, Wexford, PA (US); Anthony D. Shoemaker, Pittsburgh, PA (US)

(73) Assignee: Pestco, Pittsburgh, PA (US)

( * ) Notice: Subject to any disclaimer, the term of this patent is extended or adjusted under 35 U.S.C. 154(b) by 887 days.

(21) Appl. No.: 11/805,662

(22) Filed: May 24, 2007

(65) Prior Publication Data

US 2008/0292508 A1 Nov. 27, 2008

(51) Int. Cl.
*A61L 9/04* (2006.01)

(52) U.S. Cl. .......................... 239/34; 239/54; 239/51.5; 239/57; D23/366; D23/367; D23/368; D23/369; 422/120; 422/123; 392/386; 392/390; 392/394

(58) Field of Classification Search ...... 422/5, 422/120, 123; 239/34, 51.5, 54, 57; 392/386, 392/390, 394; D23/366, 367, 368, 369
See application file for complete search history.

(56) References Cited

U.S. PATENT DOCUMENTS

| | | | |
|---|---|---|---|
| 2,481,296 A | 9/1949 | Dupuy | |
| 2,723,158 A | 11/1955 | Molina | |
| 4,035,451 A | 7/1977 | Tringali | |
| 4,294,778 A | 10/1981 | DeLuca | |
| 4,857,240 A | 8/1989 | Kearnes et al. | |
| 4,931,258 A * | 6/1990 | Zlotnik et al. | 422/124 |
| 5,147,582 A | 9/1992 | Holzner, Sr. et al. | |
| 5,223,182 A | 6/1993 | Steiner et al. | |
| 5,431,885 A | 7/1995 | Zlotnik et al. | |
| 5,613,625 A | 3/1997 | Specht | |
| 5,707,499 A | 1/1998 | Joshi et al. | |
| 5,744,014 A | 4/1998 | Gordon et al. | |
| 5,765,751 A | 6/1998 | Joshi | |
| 5,871,153 A * | 2/1999 | Doggett, Jr. | 239/34 |
| 5,932,204 A | 8/1999 | Joshi | |
| 6,109,539 A | 8/2000 | Joshi et al. | |
| 6,283,461 B1 | 9/2001 | Joshi et al. | |
| 6,491,684 B1 | 12/2002 | Joshi et al. | |
| 6,575,961 B2 | 6/2003 | Joshi | |
| 6,787,008 B2 | 9/2004 | Joshi et al. | |
| 6,923,383 B1 | 8/2005 | Joshi et al. | |
| 6,931,202 B2 * | 8/2005 | Pedrotti et al. | 392/395 |
| 6,957,779 B2 | 10/2005 | Joshi et al. | |
| 7,149,417 B2 | 12/2006 | Joshi et al. | |
| D552,225 S * | 10/2007 | Borovicka et al. | D23/364 |
| 2004/0261790 A1 | 12/2004 | Joshi et al. | |
| 2005/0126912 A1 | 6/2005 | Theeuwes et al. | |
| 2006/0052768 A1 | 3/2006 | Joshi et al. | |
| 2007/0001024 A1 | 1/2007 | Wold et al. | |

\* cited by examiner

*Primary Examiner*—Sean E Conley
(74) *Attorney, Agent, or Firm*—Clifford A. Poff; Suzanne Kikel

(57) ABSTRACT

An aromatic odor neutralizer includes a dispenser housing with an internal passage between end walls and communicating with vents in the sides for aerodynamic airflow to efficiently absorb vapors from a vaporizer chamber within the dispenser housing. The vaporization chamber contains a wick with an end part immersed in fluid in a storage cup that is gravity fed from an air tight vessel by the use of air pathways exposed when the liquid level in the cup is reduced.

23 Claims, 17 Drawing Sheets

APPARATUS FOR DISPENSING AN AROMATIC ODOR NEUTRALIZER

CROSS-REFERENCE TO RELATED APPLICATIONS

Not Applicable

BACKGROUND OF THE INVENTION

The present invention relates to construction and arrangement of parts for a dispenser apparatus providing aerodynamic air passages to communicate with an evaporation chamber in a vaporizer and, more particularly, to a gravity driven fluid supply vessel for maintaining a supply of volatile liquid in a storage cup containing an edge portion of a wick for broadcasting the volatile liquid along the evaporation chamber.

Description of the prior art: A dispenser for volatile fluid is disclosed in three related U.S. Pat. Nos. 5,533,705; 5,816,845 and 6,105,916 provides a drive selectively using a large or small motor providing an air stream for generating vapor from a wick, ceramic wafers, or discs containing vaporizable deodorant reversible mounting back to back. Socket assemblies provide a socket for a motor of larger dimensions and a socket for a motor of smaller dimensions. A frame for a cabinet composed of separate back plate, top member and bottom member of a resilient plastic so that the top member and bottom member are snap-locked to the back plate and secured further by projections from the top and bottom members in slots in the back plate. The bottom member is a liquid tight tray capable of processing deodorants in bottles through wicks or can with wicks, absorbent surcotas and wafers. There is a bottle holder snap-locked to the underside of the top member. A battery-blower assembly is snap-locked to the back plate. The battery poles are joined to the wires from the blower-motor by clips using solder less connections.

More recently as disclosed in U.S. Pat. No. 6,957,779 is a framed fluid delivery device that is made up of a fluid-delivery cartridge for the timed-release delivery of a fluid. The fluid delivery cartridge retained by a frame assembly uses a base portion for the delivery of fluid released from a cartridge. The base secures the fluid delivery cartridge within the frame assembly proximate the end when fluid is released. The fluid-delivery cartridge has a bottom, a top, and sides, and a dispersion pad positioned proximate the bottom of the fluid-delivery cartridge that at least partially surrounds the sides of the fluid-delivery cartridge. A generator to generate gas is used for powered discharge of volatile liquid from the storage cell that is part of the fluid delivery cartridge.

Accordingly, it is an object of the present invention to provide a dispenser for an aromatic odor neutralizer embodying an enhanced aerodynamic passage for the mixture of vapors of odor neutralizer fluid with an ambient air flow.

It is a further object of the present invention to provide an aromatic dispenser having side vents along an internal passage way extending between apertures in walls at the distal ends of the dispenser.

It is a further object of the present invention to provide an aromatic dispenser embodying a construction of parts to allow a chose to the desired dispersion rate of volatile liquid from a replaceable vaporizer cartridge by various means that include passive air currents, forced air by a motor driven fan, selective masking of areas an evaporation chamber supplied by a gravity driven dispenser for the volatile fluid.

It is another object of the present invention to provide a vaporizer having a cylindrical evaporation chamber containing a wick immersed in a bath of volatile liquid driven by gravity from an integral vessel wherein a controlled ingress of air is exchanged for liquid discharge of volatile liquid.

SUMMARY OF THE INVENTION

According to the present invention there is provided an aromatic dispenser apparatus including the combination of a dispenser cover including an elongated convexly-shaped central body extended at each side by spaced apart walls with a vent there between for ventilating the interior of the dispenser cover, the dispenser cover further including end walls having access openings for ventilating the elongated convexly-shaped central body, an elongated frame including a receptacle section terminating at a mounting fixture for pivotal support of the dispenser cover between an opened position and an operating position, side guards projecting from the receptacle section to traverse the vent at each side of the of the dispenser cover when in the operating position, the side guards having apertures for ventilating a volume bounded between the side guards and the receptacle section, and a vaporizer including an evaporation chamber supplied with a volatile liquid by a vessel, the vaporizer being fixedly positioned by the mounting fixture to extend between the projecting side guards to infuse air venting from the dispenser cover and side guards with vapors from the evaporation chamber.

According to a further aspect of the present invention there is provided a vaporizer for an aromatic odor neutralizer, the vaporizer including the combination of a vessel including a side wall joined with a first end wall to form a gaseous impervious chamber above a stored volume of volatile liquid bounded by a dispensing wall opposite the first end wall, a ventilating housing including a cylindrical side wall for receiving the vessel to form a vaporization chamber there between terminating at a liquid storage cup for volatile liquid dispensed from the vessel, a metering wall encircling the dispensing wall, the metering wall having at least one opening for an intermittent flow of air into the gaseous impervious chamber counter concurrent with a discharge of volatile fluid from the vessel to the liquid storage cup, an upstanding surface in the liquid storage cup for piercing the dispensing end wall, and a wick having a portion immersed in volatile liquid in the liquid storage cup while residing in the vaporization chamber.

According to a preferred form of the vaporizer embodying the present invention there is provided the combination of a vessel for dispensing a volatile liquid, a vessel cap to allow access to liquid storage compartment of the vessel and forms an airtight seal with the vessel, the vessel cap being non reversible thread connected by interfering flexible prongs on mating threads that seat to prevent unthreading of the vessel cap, a weaken end wall in a protruding sleeve section at end of the vessel opposite the cap, a rectangular wick fashioned into a cylinder without creases, a cylindrical sidewall of the vessel contains spaced apart protruding rings that protrude to vary heights such that largest protruding height resides at the liquid discharge end of the vessel for stabilizing the position of the wick when encircling the vessel, the cylindrical sidewall extends to a metering portion having openings dispersed about the terminal edge for counter concurrent flows of air and volatile fluid, and a ventilating housing with a cup at one end forming a reservoir for volatile liquid dispensed from the vessel, a knife edge upstanding from the bottom wall of the cup for piercing the weaken end wall, the end of the housing opposite the cup having a snap ring for fixedly positioning the cap of the vessel to form a evaporation chamber containing the wick spaced about the cylindrical wall of the housing.

BRIEF DESCRIPTION OF THE SEVERAL VIEWS OF THE DRAWINGS

The present invention will be more fully understood when the following description is read in light of the accompanying drawings in which.

DETAILED DESCRIPTION OF THE INVENTION

Figure 3:
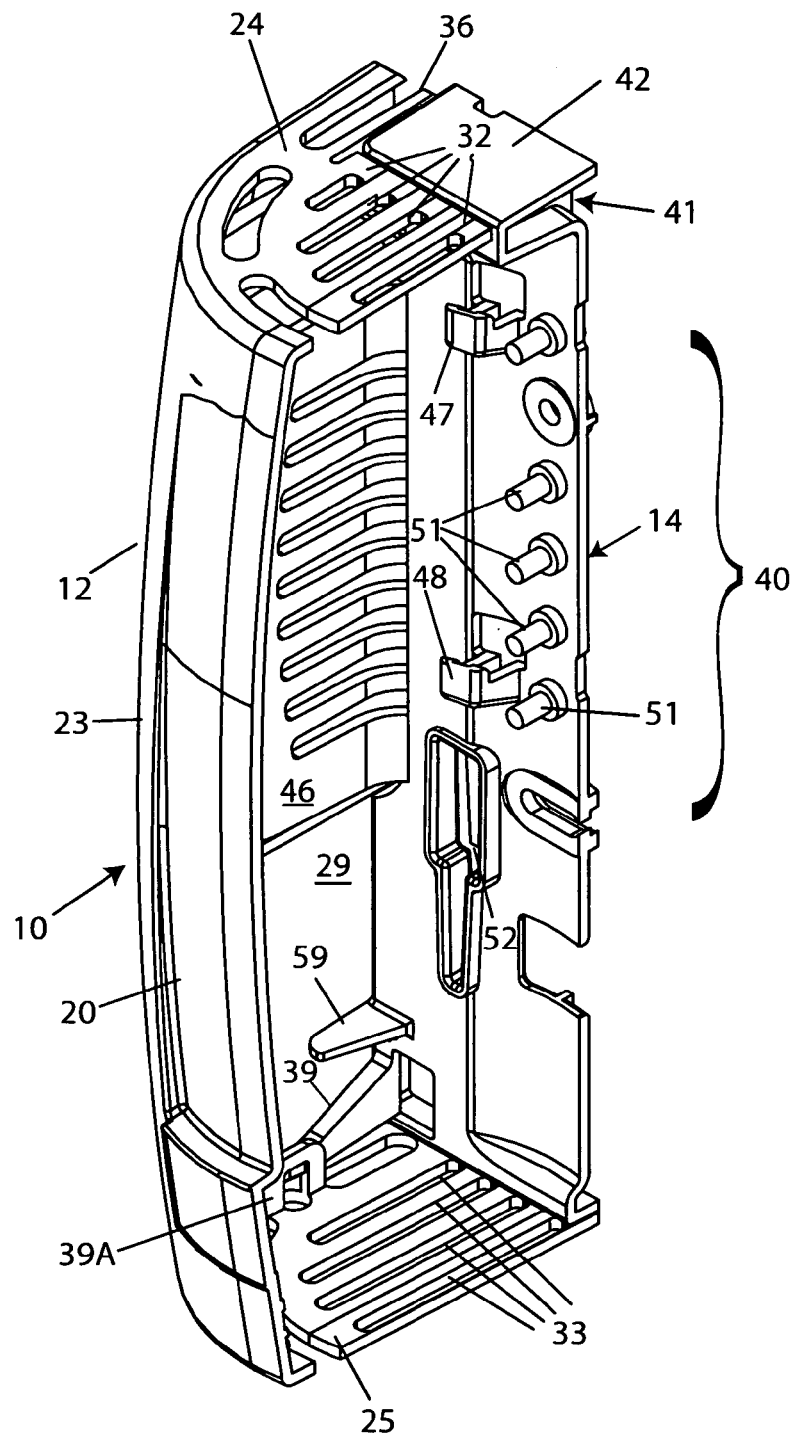
FIG. 3 is a sectional view taken along lines III-III of FIG. 1 with the vaporizer and fan units removed.
Figure 4:
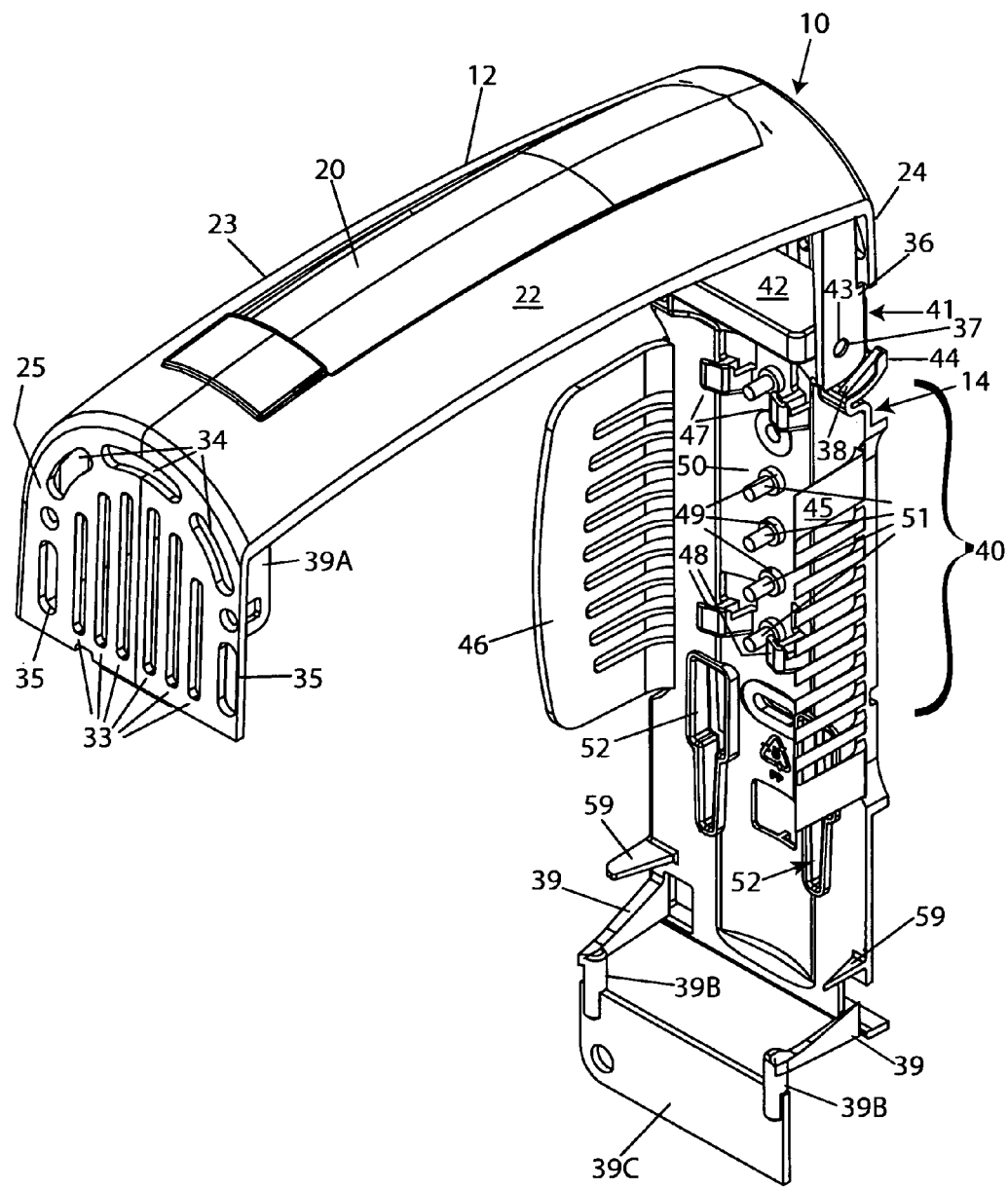
FIG. 4 is a sectional view taken along lines IV-IV of FIG. 1 with the dispenser cover moved to an open position and the vaporizer and fan units removed.
Figure 5:
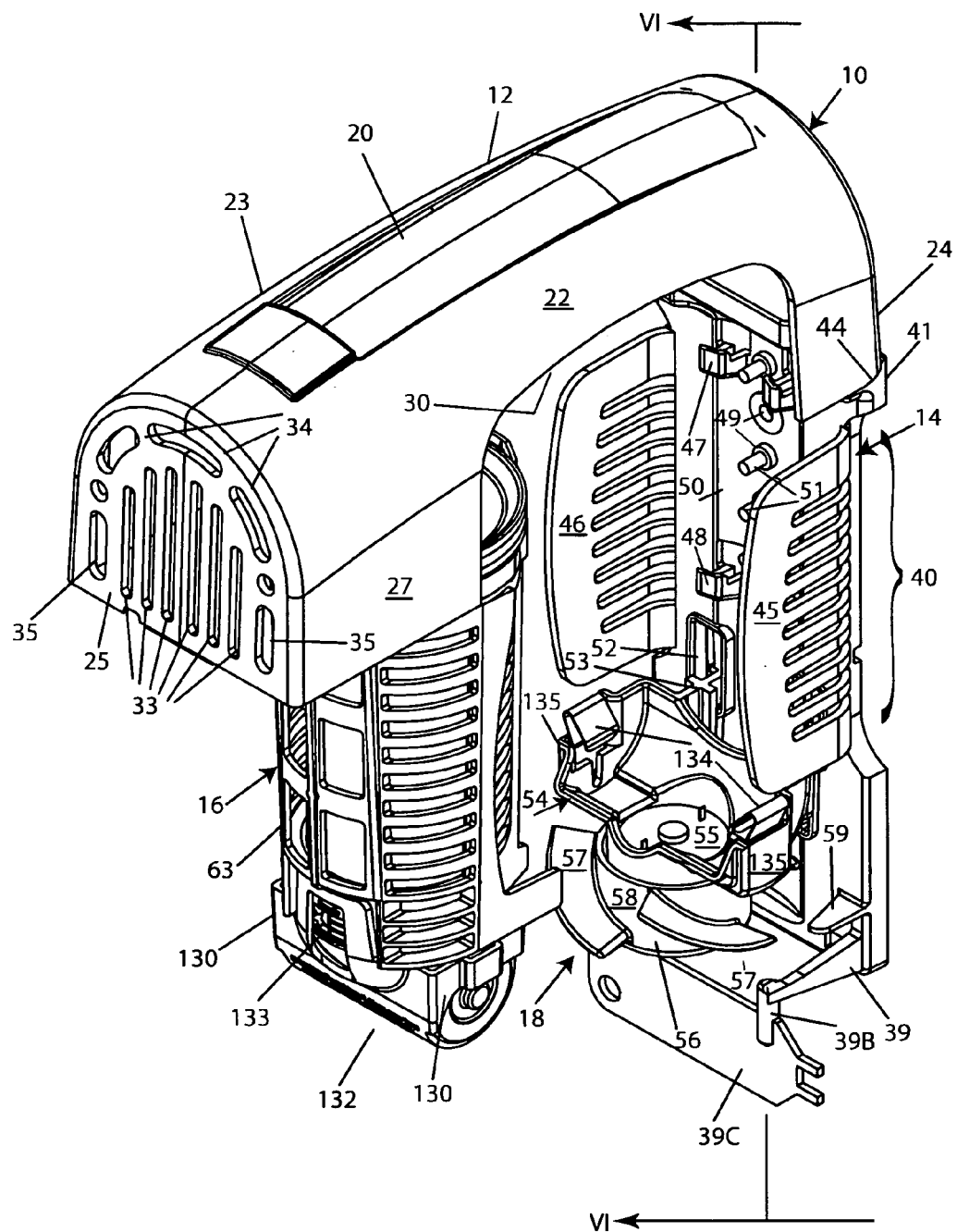
FIG. 5 is a frontal isometric view of the preferred embodiment of apparatus according to the present invention with the dispenser cover located in an open position and the vaporizer remote to an operating position and the fan unit installed.

FIGS. 1-6 illustrated the preferred embodiment of an aromatic dispenser apparatus 10 that includes according to the present invention a dispenser cover 12 pivotally joined to a dispenser frame 14 constructed to receive fasteners, not shown and well known in the art, to secure the an aromatic dispenser apparatus to vertical wall surface of the room or other structure. The dispenser frame 14 is constructed to carry a vaporizer 16 and, if desired, the option of a fan module 18 (FIG. 5).

The dispenser cover 12 is made up of a central body 20 that is elongated and convexly shaped in the direction of the elongated length. Body sidewall sections 22 and 23 are continuous along the opposed longitudinal sides of the central body 20 and define therewith a longitudinal cavity arranged to extend between top and bottom end walls 24 and 25 for forming a convection guide for airflow to each of the end walls. Body sidewall sections 22 and 23 are continuous along the opposed longitudinal sides with spaced apart walls 26, 27 and 28, 29, respectively. The spaced apart walls 26, 27 and 28, 29 together with the sidewall sections and the central body 20 take the form of circular ring sector shaped walls that form part of the elongated convexly shaped central body. Vents 30 and 31 at opposite sides of the central body ventilate the interior of the dispenser cover. Vent 30 is bounded by an edge portion of side wall section 22 and by opposite sides by walls 26 and 27. Vent 31 is bound along an edge portion of side wall section 23 and at opposite sides by walls 28 and 29. The top and bottom end walls 24 and 25 each have an array of parallel slots 32 and 33, respectively, bounded by a semicircular perimeter section containing curved slots 34 and terminal slots 35. The lengths of the parallel slots 32 in the top wall 24 as compared with the parallel slots 33 in the bottom wall 25 are reduced to provide a cavity bounded by spaced parallel arms 36 extending in interior of the convexly shaped central body 20 where each arm contains an aperture 37 in the extended end portion terminating at an curved end wall 38 forming a cam locking surface for pivotally mounting of the dispenser cover 12 to the dispenser frame 14. As shown in FIGS. 3, 4 and 5 when the dispenser cover 12 is pivoted to the operative position, i.e. seated against to dispenser frame 14, parallel arms 39 with hooked ends extend parallel with the lengths of the bars from the interior of the central body 20 for locking engagement with resilient latch bars 39A extending from the lower portion of the dispenser frame 14 and terminating with lateral hooked ends. The resilient lock bars 39A are displaced from locked engagement with the arms 39 by spaced bars 39B on a key 39C. Appropriately spaced openings in the end wall 25 pass the bars 39B into an engagement with free ends of the lock bars 39A and deflect the hooked ends of the bars from last engagement with the ends of arms 39.

Figure 1:
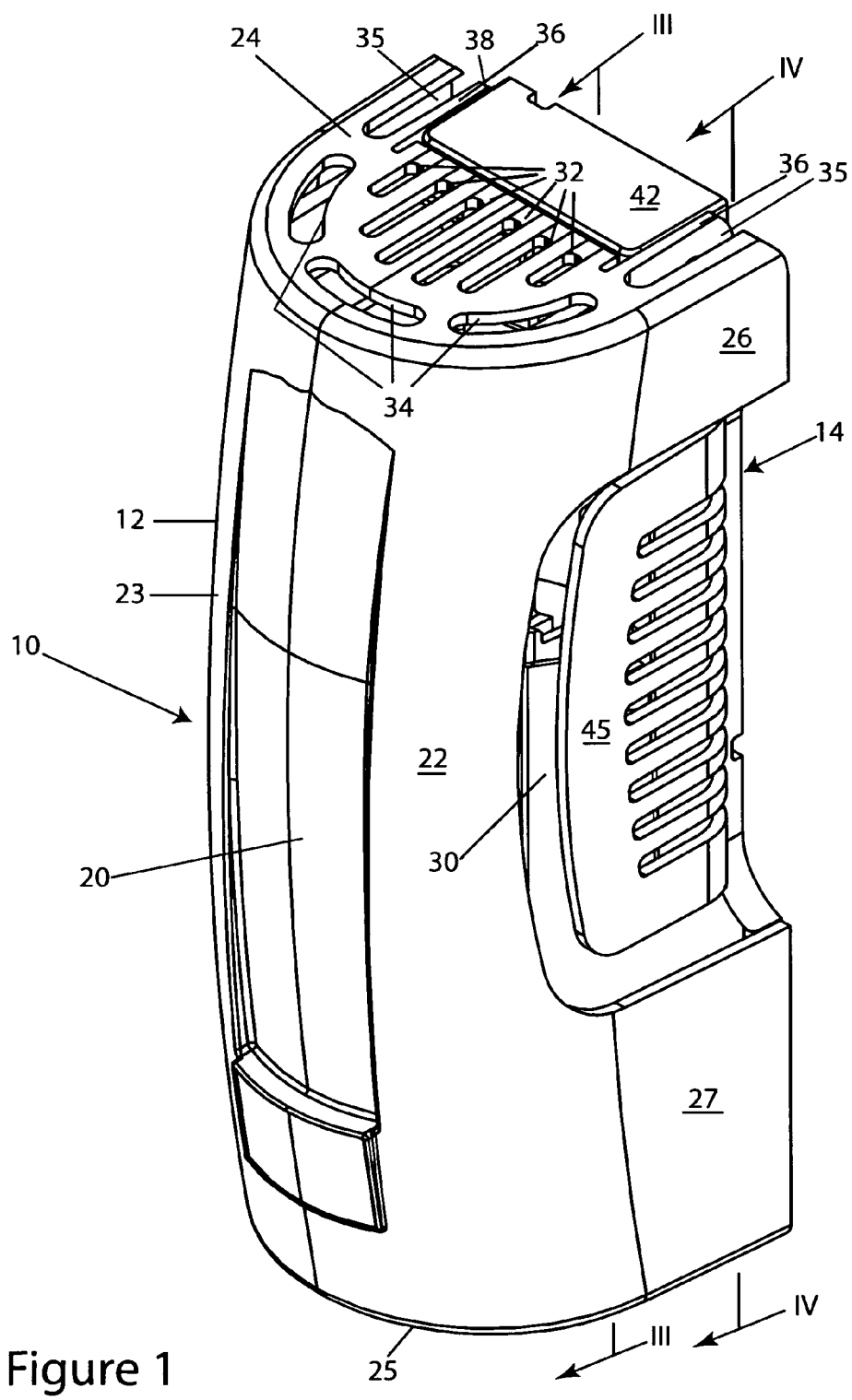
FIG. 1 is a frontal isometric view of the preferred embodiment of apparatus according to the present invention for dispensing an aromatic odor neutralizer in the operative position of the component parts.
Figure 2:
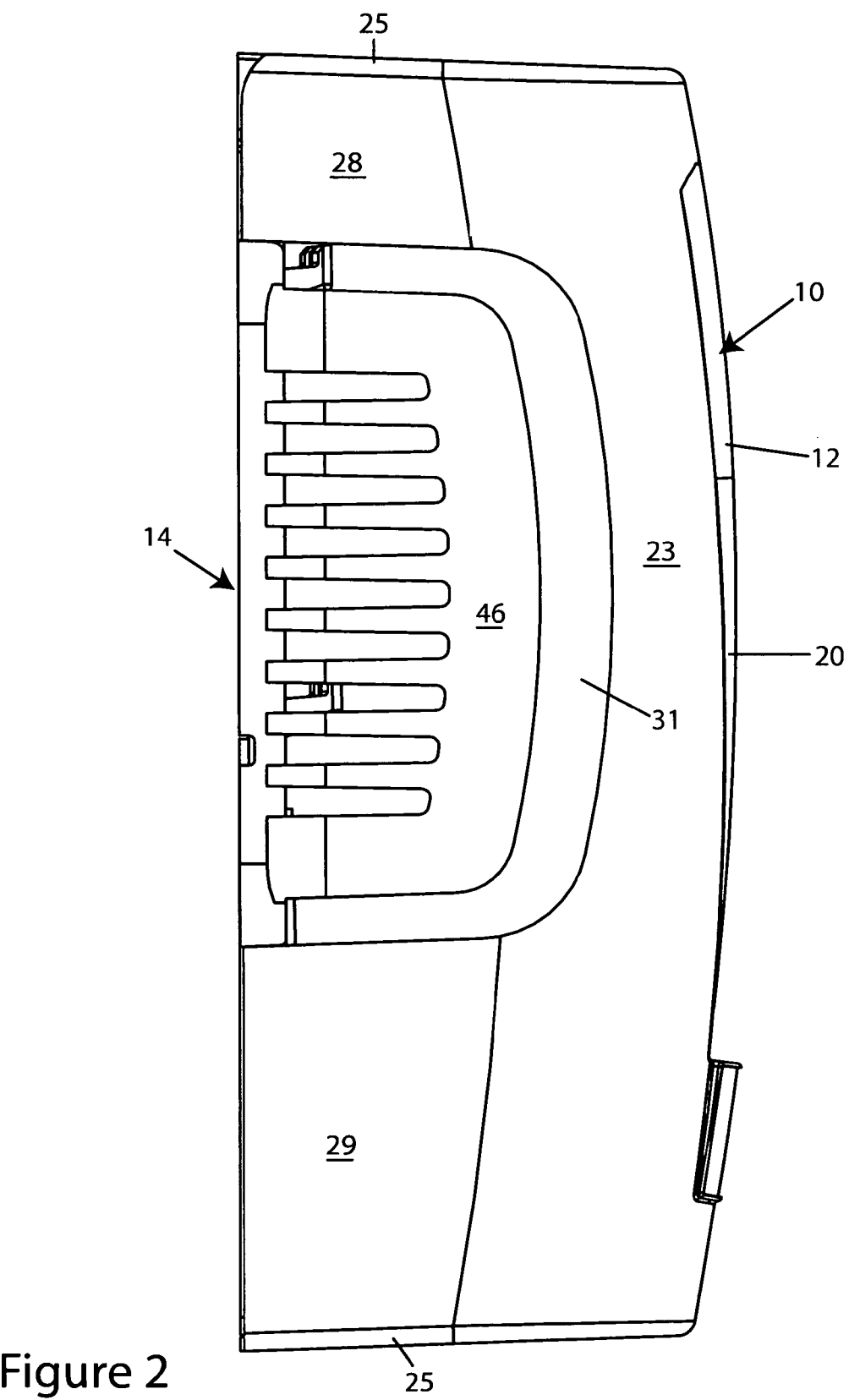
FIG. 2 is a left side elevation view of the apparatus shown in FIG. 1.

The dispenser frame 14 takes the form of an elongated structure embodying a construction to form a receptacle section 40 terminating at a mounting fixture 41 for pivotal support of the dispenser cover 12 between the opened position shown in FIGS. 4 and 5 and an operating position shown in FIGS. 1-3. The mounting fixture 41 takes the form of a rectangular block 42 contains a hinge pin 43 extending from each of the opposite lateral sides to extend into the aperture 37 in the extended end portion of the arms 36. The pivotal movement of the dispenser cover is controlled and limited by sliding contact between the curved end walls 38 along pressure bearing plate sections 44 that serve to hold the cam locking surface formed on the ends of the curved end walls 38 for pivotally mounting of the dispenser cover 12 to the dispenser frame 14. Side guards 45 and 46 project from the receptacle section 40 to traverse the vents 30 and 31 at the sides of the dispenser cover 12 when in the operating position. The side guards 45 and 46 are bounded in a spaced relation by the sidewall extensions 26, 27 and 28, 29, which are coextensive with the end walls, and define opposed boundary edges of the vents.

The side guards have apertures 45 and 46 for the passage of air currents and thereby ventilate a volume bounded between the side guards 45 and 46 and the receptacle section 40 wherein the vaporizer 16 is fixedly positioned by upper and lower spaced pairs of support hangers 47 and 48 to extend in a spaced apart relation between the projecting side guards. As best shown in FIG. 5, the side guards 45 and 46 will overlie an evaporation chamber in the vaporizer 16 when mounted on the receptacle section for exposing the vents at the sides of the dispenser cover 12 to ventilate vapors from the evaporation chamber.

Figure 6:
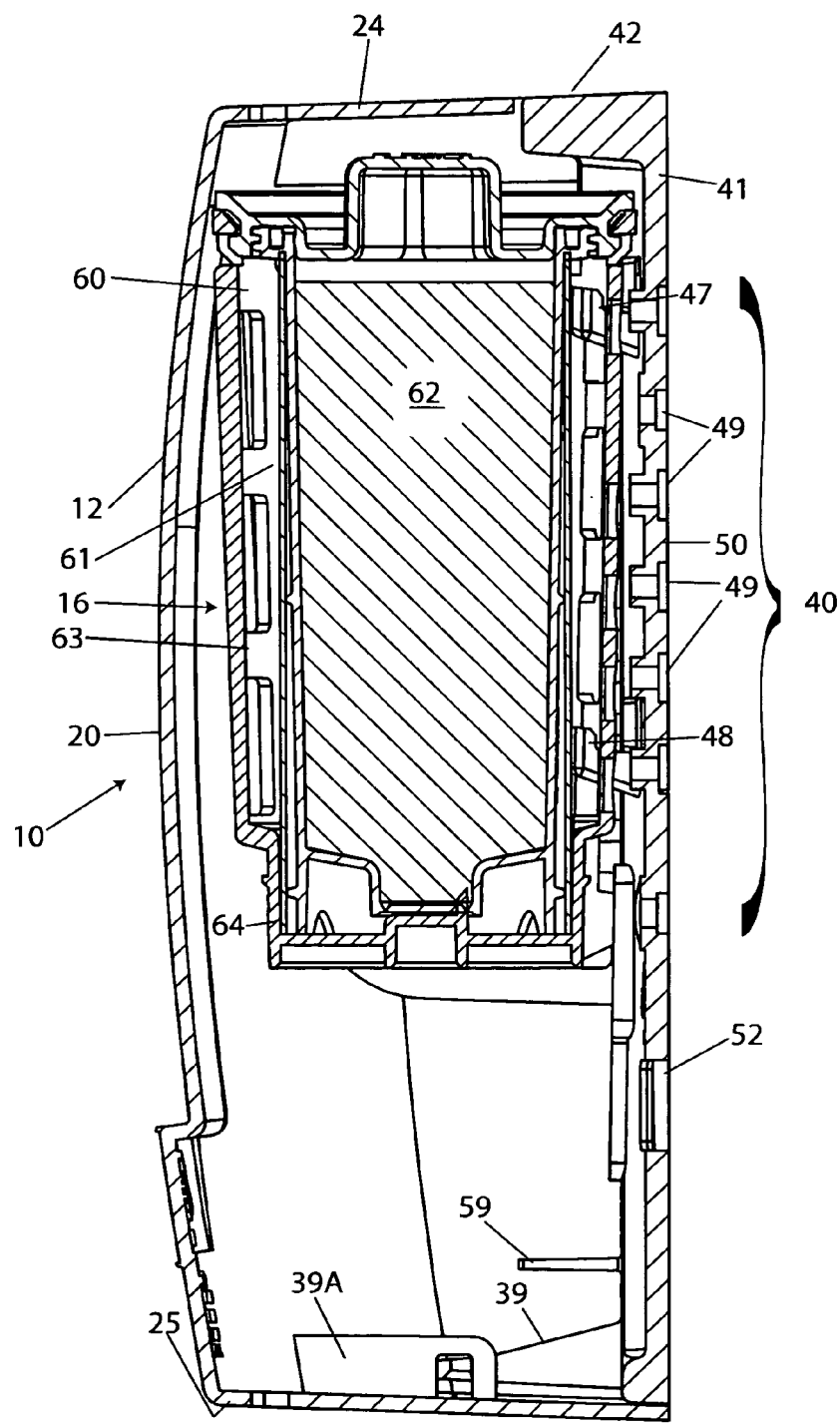
FIG. 6 is a sectional view taken along lines VI-VI of FIG. 5 with the vaporizer and fan units installed according to the preferred embodiment of the present invention.

As shown in FIG. 6, the interconnected relation between the vaporizer 16 and the receptacle section 40 is controlled by a proprietary array arrangement of key apertures 49 formed in a grid plate section 50 of the vaporizer for a go/no go inter engaging relationship with a protruding array of keys 51 mounted in the receptacle section 40. Underlying the receptacle section 40 are parallel T-shaped apertures 52 for interlocking engagement with enlarged heads of latch bars 53 extending from a drive frame 54. The drive frame has a molded configuration with a cavity to receive a motor 55 for driving fan blade assembly 56 mounted on the shaft of the motor to produce an air stream along the elongated convexly shaped central body of the dispenser cover 12. The fan blade assembly 56 includes helically arranged fan blades 57 extending from an annular sidewall of a hub 58. The fan blades 57 are orientated on the hub 58 so as to create an up draft of air when driven by the motor. Guide bars 59 project from opposite lateral sides of the dispenser frame 14 to stabilize and guide the dispenser cover 12 during pivotal movement to the closed position.

The vaporizer 16, as shown in FIGS. 6-10, includes evaporation chamber 60 having an elongated tubular configuration and the side guards 45 and 46 as show in FIG. 5 have concave configurations transverse to the extended length of the evaporation chamber to partly wrap in an outwardly spaced relation about the evaporation chamber and thereby maximize the exposure of the ambient air flow to the volatile liquid conducted by a wick 61. The wick is a rectangular fibrous sheet of porous material fashioned into a cylinder without creases to reside in the evaporation chamber formed as a cylindrical cavity between a vessel 62 containing the supply of volatile liquid and a cylindrical ventilating housing 63 with a liquid storage cup 64 at one end forming a reservoir for volatile liquid dispensed from the vessel 62. A portion of the wick 61 is immersed in volatile liquid in the liquid storage cup 64 while residing in the vaporization chamber. The cylindrical shape of the ventilating housing 63 is comprised of upright post members 65 extending from the rim of the cup 64 and dispersed about a circle defined by the rim of the cup. The rim of the cup is extended so as to prevent spillage of fluid from the interior of the cup. The post members 65 are interconnected by transverse ribs 66 forming an elongated tubular venting cage extending between the side guards 45 and 46. The post members 65 interconnected by the ribs 66 are arranged to provide that the cylindrical sidewall includes rectangular windows 66 for mounting the ventilating housing on the support hangers 47 and 48 in the receptacle section. The peripheral sidewall of the ventilating housing 63 includes parallel and radically outward extending stabilizer bars 68 to engage with the receptacle section when mounting the vaporizer to the elongated frame.

Figure 7:
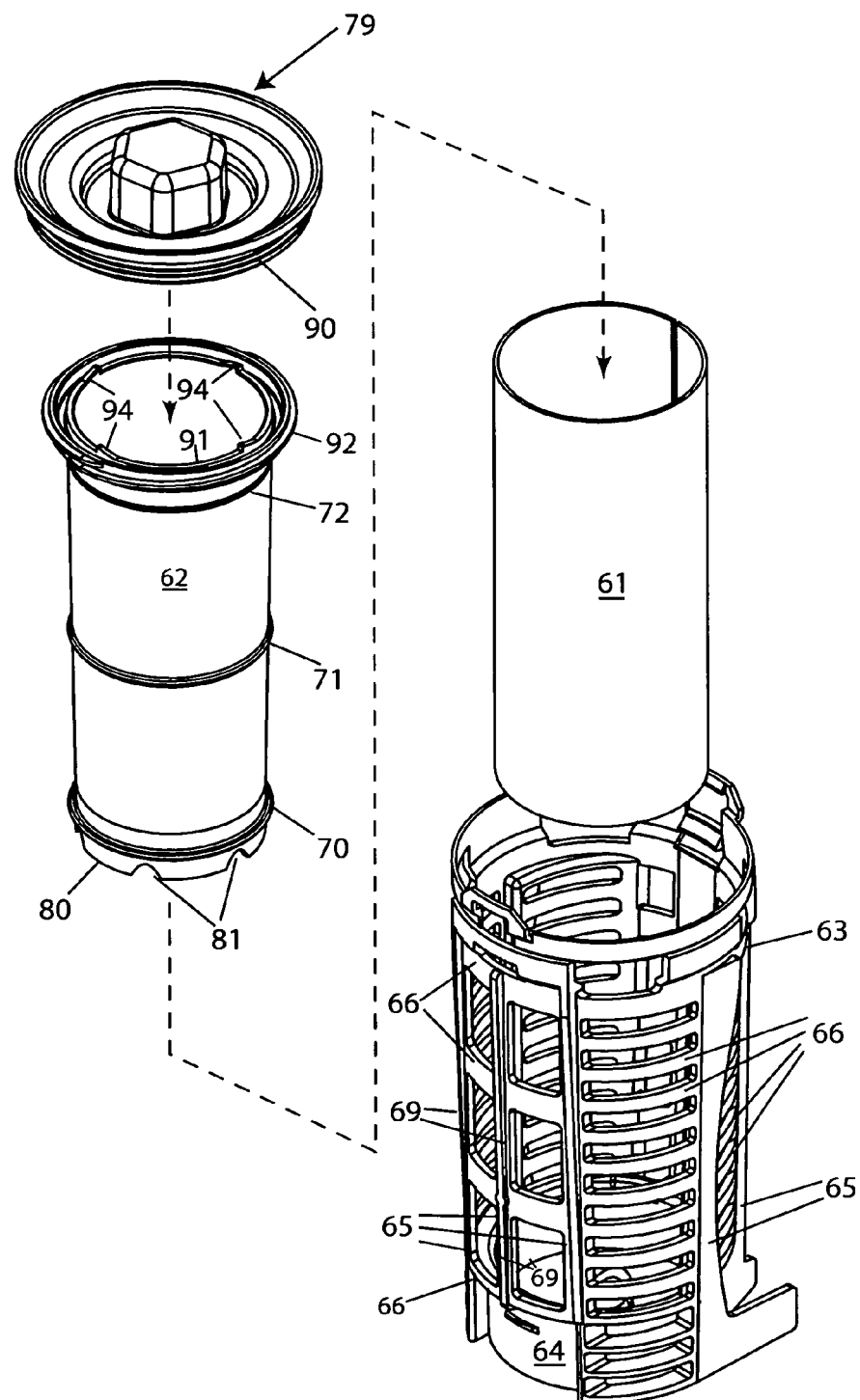
FIG. 7 is an exploded isometric view of the vaporization unit according to the present invention.
Figure 8:
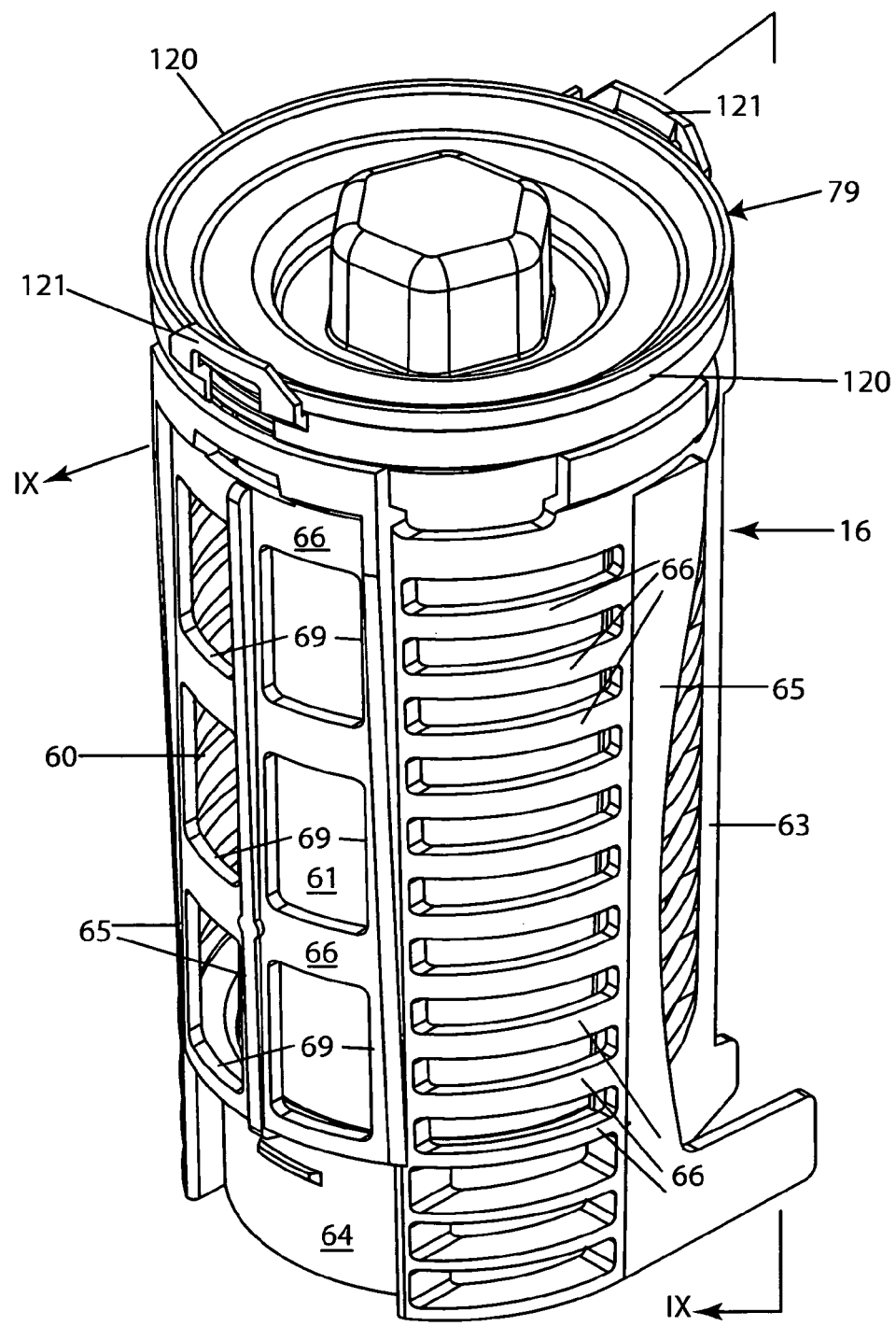
FIG. 8 is an isometric view of the vaporization unit shown in FIG. 7 in a preassembled state.
Figure 9:
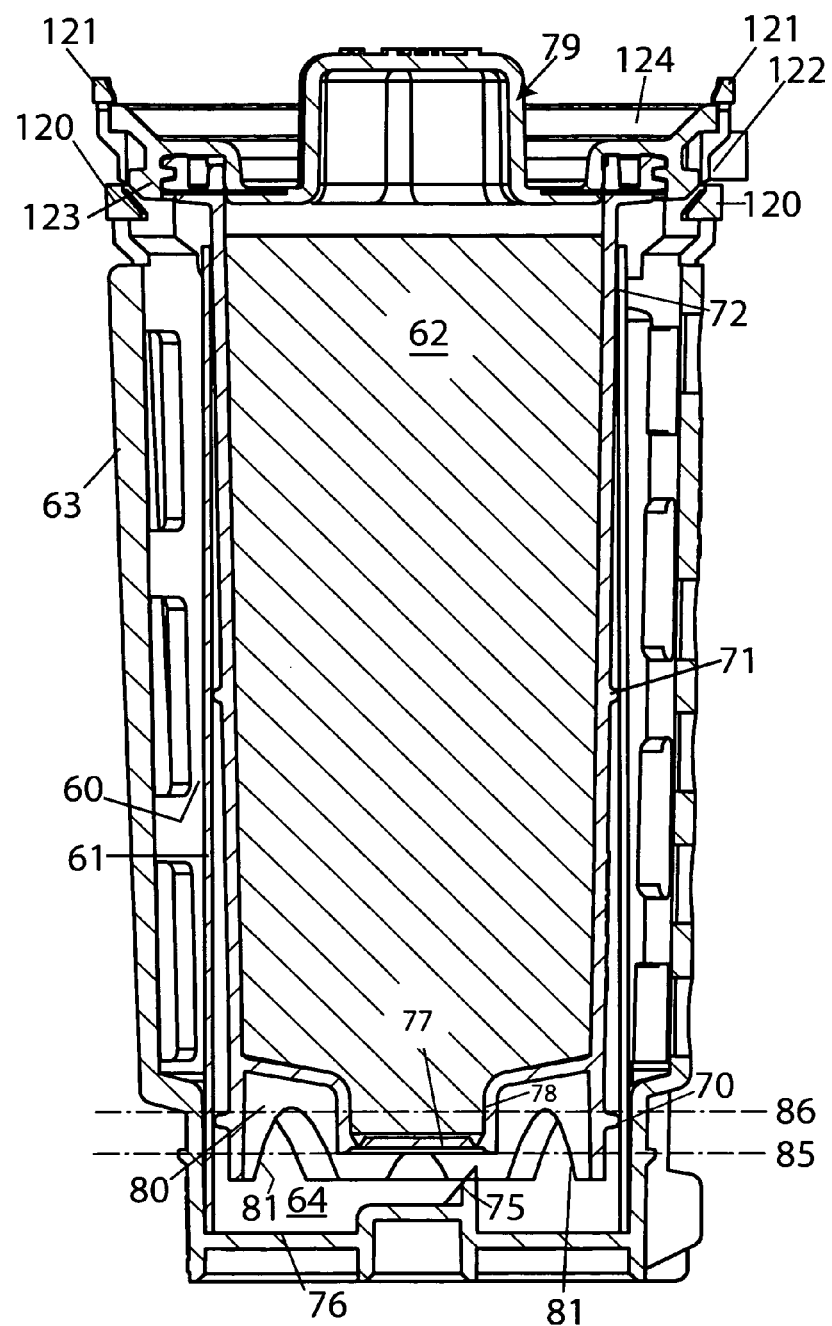
FIG. 9 is a sectional view taken along lines IX-IX of FIG. 8 illustrating the arrangement of parts of the vaporizer prior to an operative state for dispensing volatile liquid.

As shown in FIGS. 7-11, the construction of the venting housing 63 produces an array venting windows 69 confronting the elongated convexly shaped central body of the dispenser cover 12. Preferably, the sidewall of the vessel 62 or alternatively, the vessel 62 includes at least one wick support ring 70 in the vicinity of the cup 64 to maintain a desired spacing between of the wick from the confronting walls forming the evaporation chamber. Most desirably there are spaced apart rings protruding from a sidewall into the evaporation chamber for spacing the wick from the vessel. As shown in FIGS. 6, 7 and 9 three spaced apart rings 70, 71 and 72 from the vessel 62 protrude at varying heights with the greatest height located at the liquid discharge end of the vessel for spacing said wick from said vessel and stabilizing the wick in vaporization chamber.

Figure 17:
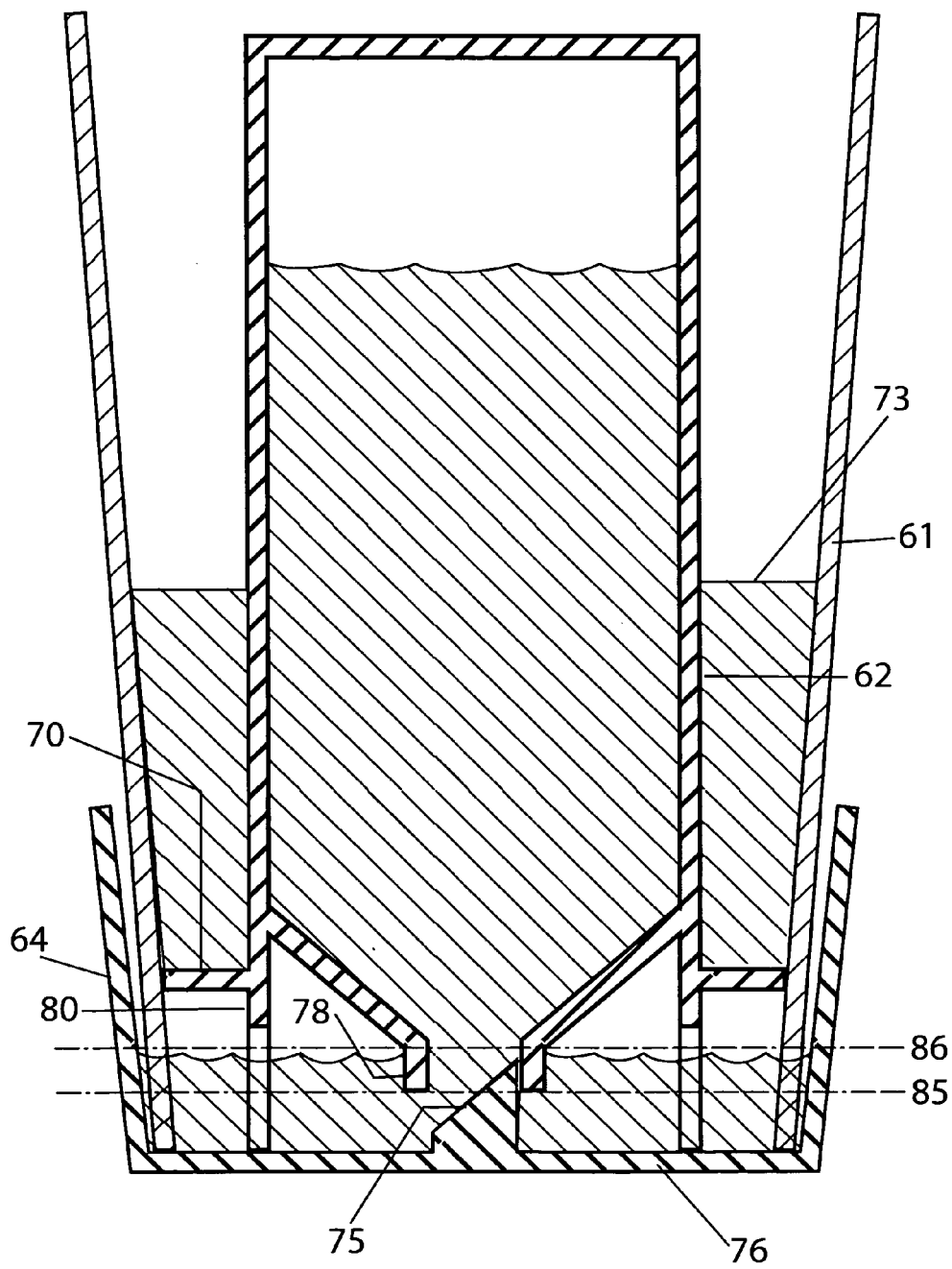
FIG. 17 is a schematic illustration of the relation of parts during vaporization of volatile liquid according to the present invention.
Figure 18:
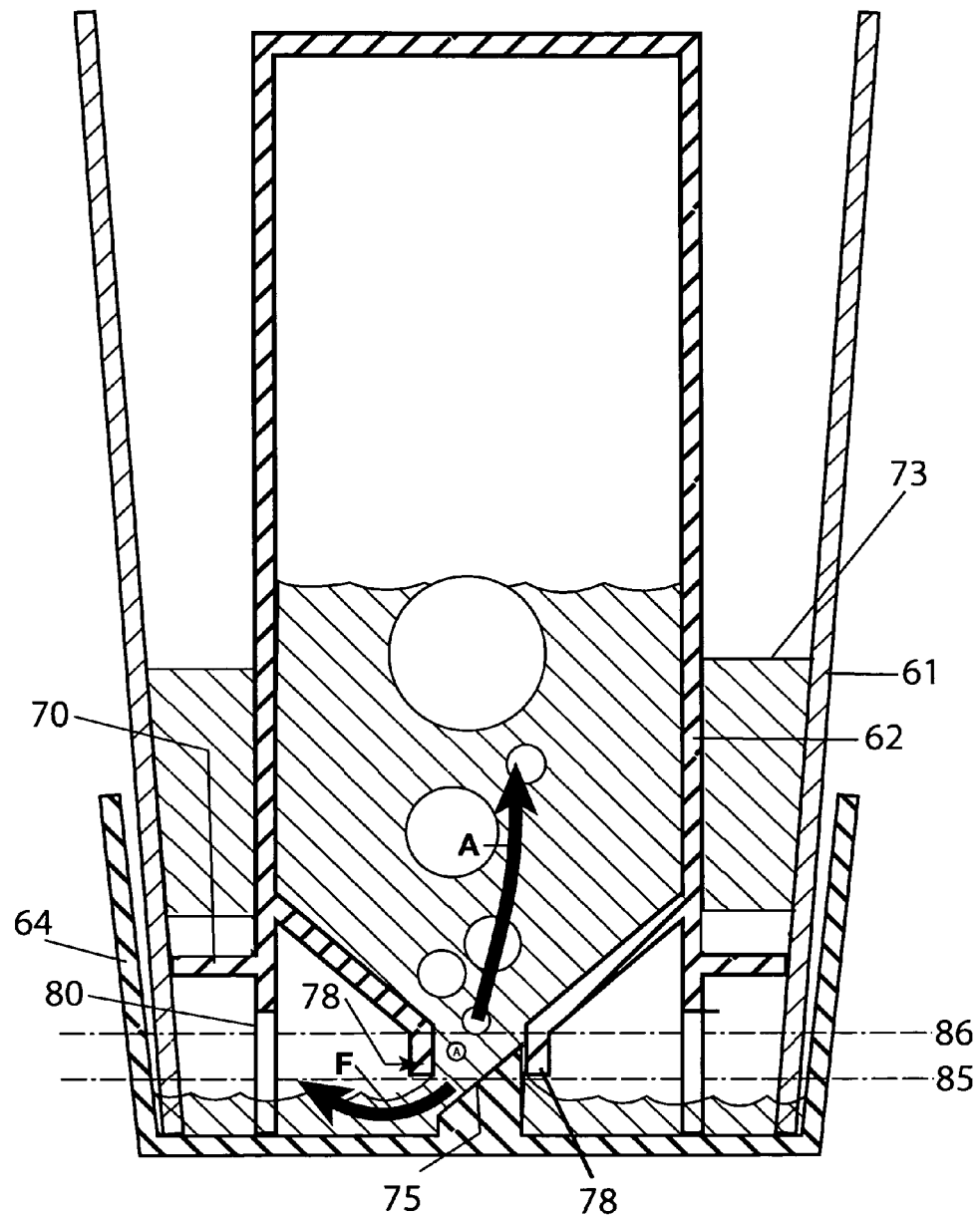
FIG. 18 is a schematic illustration of the relation of parts during flow of volatile liquid into a storage cup pf the vaporizer according to the present invention.

A tubular knife edge 75 projects in an upstanding manner from a bottom wall 76 of the cup 64 for piercing a weaken end wall section 77 in a dispensing wall 78 having the form of a protruding sleeve section extending from the end of the vessel 62 opposite a vessel end cap 79, which is an optional alternative to an end wall integral with the side of the vessel. Preferably, the tubular knife edge 75 is traversed in the hollow of the tubular shape by an upstanding rib 76 in the liquid storage cup to support in a suspend fashion a fractured portion of the dispensing end wall produced by the knife edge 75 and residing in the vessel. The rib 76 angularly divides by traversing a portion of a cylinder internally to suspend a fractured part of the end wall. A metering wall 80 takes the form of a downward annular extension of the side of the vessel 62. The metering wall 80 is formed with openings 81 dispersed about the terminal edge for counter concurrent flows of air and volatile fluid. As shown in FIGS. 9, 10, 11, 17 and 18 the metering wall 80 encircles the dispensing wall 78. The metering wall 80 has at least one opening, for an intermittent flow of air into the gaseous impervious chamber formed within the vessel above the volume of volatile stored therein counter concurrent with a discharge of volatile fluid from the vessel to the liquid storage cup. The dispensing wall 78 extends to a dispensing plane 85 recessed from a normally submerged metering plane 86 in the liquid contained in the storage cup. Preferably, the metering wall 80 includes a plurality of openings 81 extending in a direction proceeding from the normally submerged metering plane 86 beyond the dispensing plane 85 for establishing the dispensing plane. As shown in FIGS. 17 and 18 when the fluid level in the cup 64 is depleted by the operation of the wick 61 to a level below the metering plane 86 openings 81 serve to control an intermittent flow of air by arrow A into the gaseous impervious chamber counter concurrent with a flow of volatile fluid by arrow F from the vessel to the liquid storage cup as shown in FIG. 18.

Figure 12:
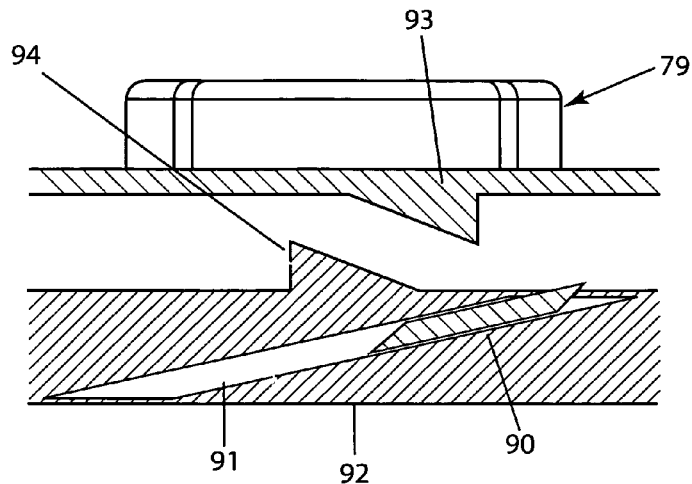
FIGS. 12, 13 and 14 schematically illustrate the operational sequence of the locking barbs for installing the locking cap on the vessel.
Figure 13:
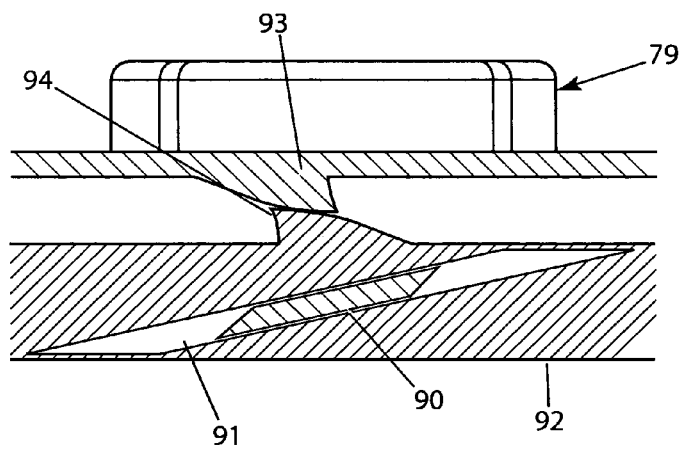
Figure 14:
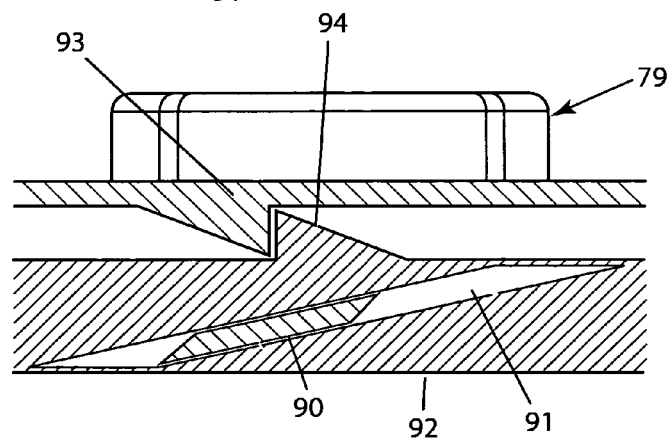

As shown in FIGS. 7 and 11-14 the provision of a flanged vessel end cap 79 allows the access to a liquid storage compartment of the vessel 62 for the introduction of the volatile liquid into the vessel and forms an airtight seal with the vessel. The vessel end cap has threads 90 that engage with mating threads 91 on a rim portion 92 of the vessel. To prevent unwanted access to the storage chamber in the vessel, unthreading of the vessel end cap is prevented by the provision of upstanding barbs 93 at spaced intervals along the screw threads 90 corresponding to intervals of upstanding barbs 94 along the mating screw thread 91 on annular side wall formed by the rim portion 92. The operation of the cap moved into a locked vacuum tight condition on the vessel is diagrammatically illustrated by FIGS. 12, 13 and 14. As shown in FIG. 12 projecting from the threads 90 on the cap are the barbs 93 and the threaded relationship with the threads 91 on the vessel operate to move the barb 94 into a confronting relationship with barbs 92. FIG. 13 illustrates that travel of the threads 90 along the threads 91 cause the barbs 93 to collide with the barbs 94 and deform due to the elasticity of the plastic material forming the vessel and the vessel cap. The deformation eventually gives way to the passage of the barbs beyond the collision site. As shown in FIG. 14 after the barbs 93 and 94 pass each other the elastic property of the material forming the barbs allow a restoration of the original shape so that the barbs confront one another in an interlocking relation and thereby prevent movement in the reverse direction to the direction traveled into the locked positions.

Figures 15, 16:
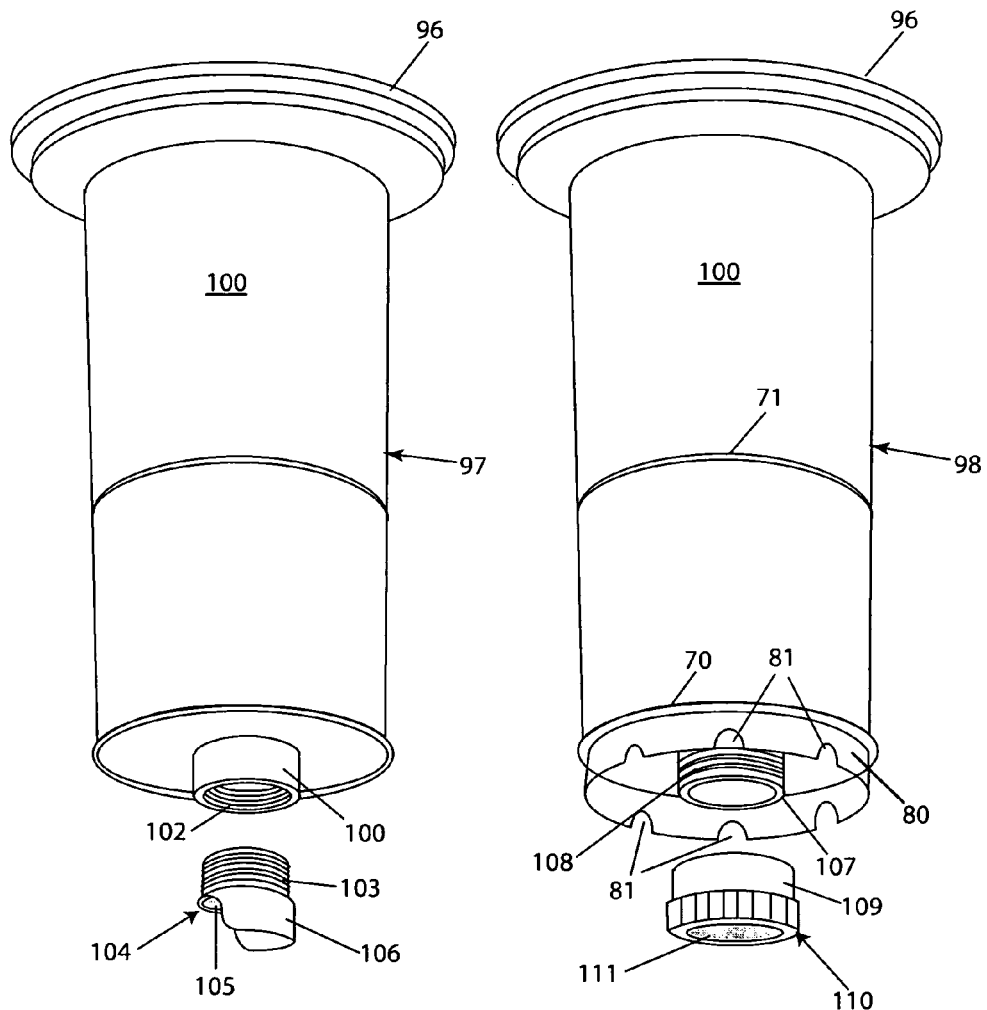
FIG. 15 is an isometric view of an alternative embodiment of storage vessel for dispensing volatile liquid for the vaporizer according to the present invention.
FIG. 16 is an isometric view of a further alternative embodiment of storage vessel for dispensing volatile liquid for the vaporizer according to the present invention.

In the embodiments of the vessel according to the present invention shown in FIGS. 15 and 16, a flanged top end wall 96 of the vessels 97 and 98, respectively, is integrally formed with the side wall 100 to provide the gaseous impervious chamber above a stored volume of volatile liquid in each of the vessels. The protruding sleeve section 101 of the vessel 97 shown in FIG. 15 is provided with internal threads 102 to receive external threads 103 on a closure cap 104 containing a pierceable sealed film or membrane 105 from which there projects a metering wall 106 comprise of a half divided tube segment forming a protruding semicircular guard wall. The protruding sleeve section 107 of the vessel 98 shown in FIG. 16 is provided with external threads 108 to receive internal threads in a rim 109 of a closure cap 110 containing a pierceable sealed film or membrane 111. The side wall of the vessel is continued by the projecting metering wall 80 having the opening 81 dispersed about the terminal edge for counter concurrent flows of air and volatile liquid as described herein above.

Figure 10:
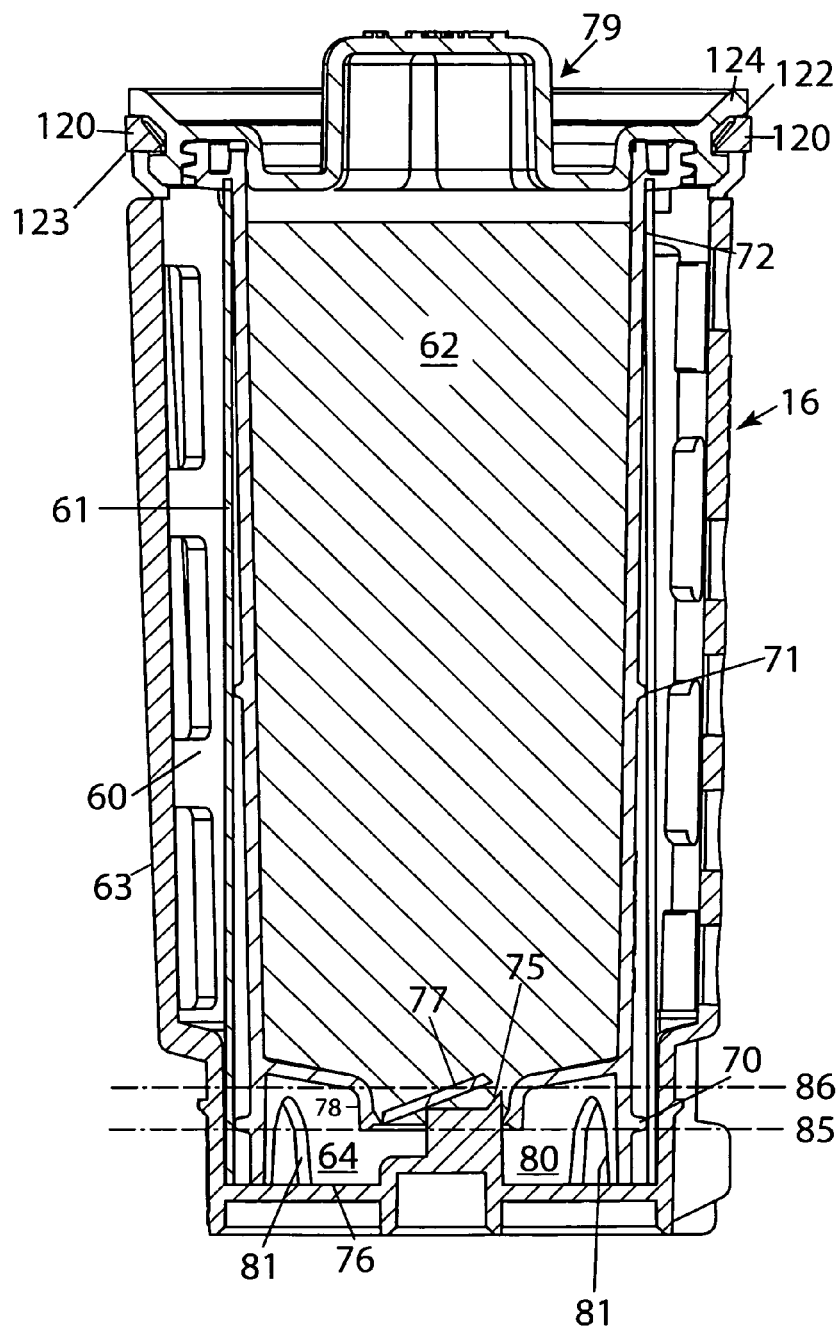
FIG. 10 is a sectional view similar to FIG. 9 and illustrating the arrangement of parts of the vaporizer in an operative state for dispensing volatile liquid.
Figure 11:
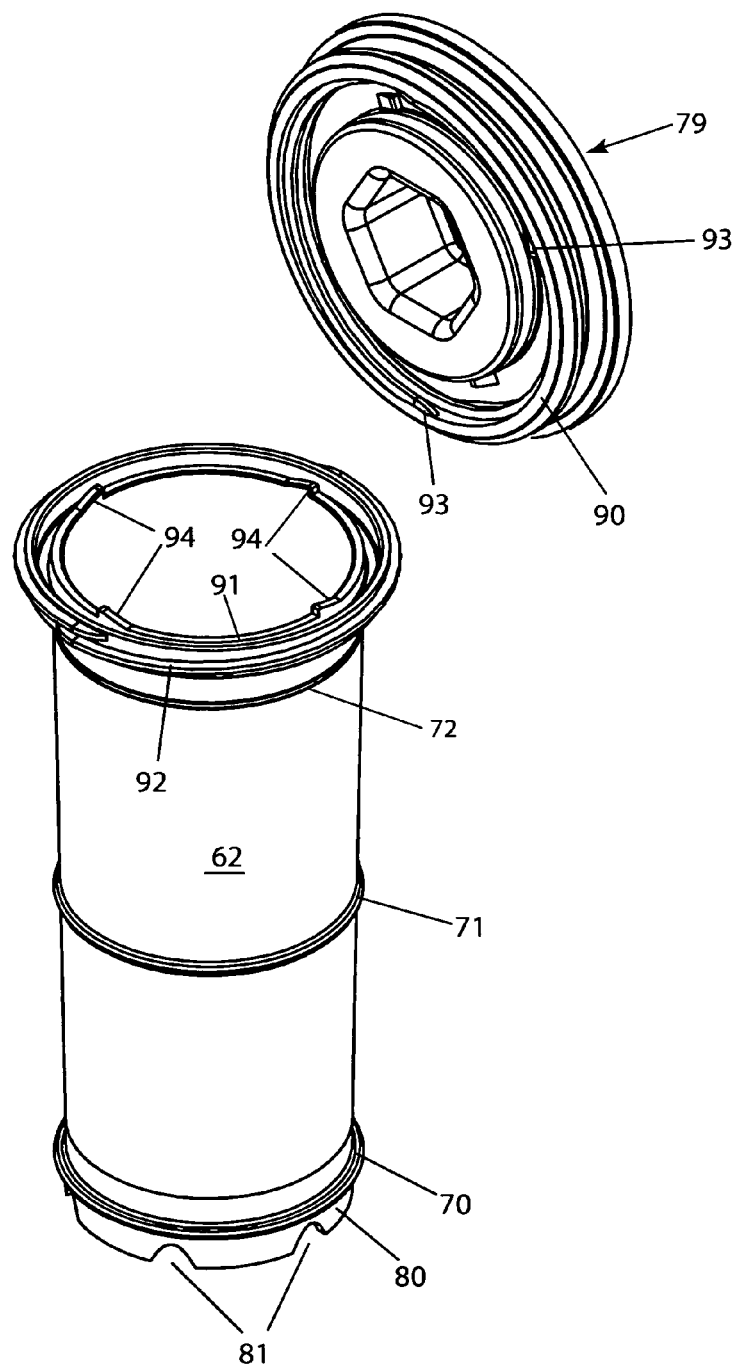
FIG. 11 is an isometric view illustrating the vessel and cap for supplying volatile fluid.

As shown in FIGS. 8, 9 and 10, the ventilating housing 63 further includes snap ring segments 120 to engage and release each of the cavities located in a flanged portion 124 of the end cap 79 of the vessel 62 and top walls 96 at the end of the vessels 97 and 98 which are remote to the vessel ends constructed to dispense volatile liquid. The snap ring segments 120 fixedly position the metering wall at the dispensing end of the vessel at a predetermined spacing from floor of the liquid storage cup 64. Diametrically opposed tear segments 121 are between snap ring segments 120. The tear segments 121 are joined to the snap ring segments by weakened walls that are easily fractured for removal to allow flexing of the snap ring segments when positioning the flanged end of the vessel between said snap ring segments. The snap ring segments 120 include a truncated conical support surface 122 that receives in a confronting relation a mating truncated conical surface 123 formed on the flanged portion of the end caps 79 and top wall 96 for suspending the vessel in the evaporation chamber. The vaporizer of the present invention is quickly replaced by removing the flange portion 124 of the cap 122 from the snap ring segment 120 and then inserting a replacement vaporizer by inserting the flange 124 in the snap ring segments as described herein above. The typical time for a total vaporization of the fluid in a newly installed vaporizer is 60 days with passive airflow and typically 30 days with a forced airflow by the fan assembly.

Figure 19:
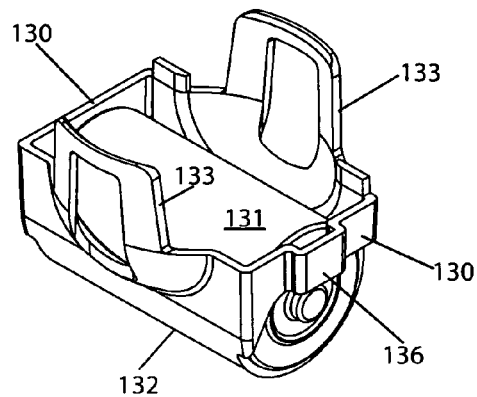
FIG. 19 is an isometric illustration of a battery holder that is optionally added to the vaporizer for powering a motor driven fan.
Figure 20:
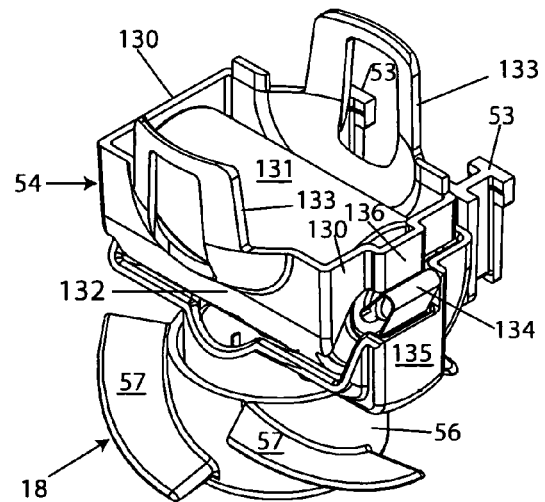
FIG. 20 is an isometric illustration of the battery holder operatively seated in the housing for the motor driven fan.

When it is desired to artificially induce an air flow in the dispenser cover, as shown in FIGS. 5, 19 and 20, a battery storage compartment is formed by opposed end walls 130 confronting pole pieces of a battery when seated against a cylindrical battery 131 container wall 132 terminating at spaced apart suspension arms 133 for support by the vaporizer 16. Strips 134 of electrically conductive material extending from the drive frame 54 toward the end walls 130 for contact with pole pieces of a battery when stored in a battery container wall 132. The electrically conductive strips 134 are retained by upstanding arms 135 spaced apart sufficiently to receive the end walls of the battery storage compartment. The end walls 130 of the battery storage compartment are arranged to expose the pole pieces of a battery while traversing opposite ends thereof. The upstanding arms 135 comprise a rectangular bar traversing one end of the battery compartment and a rectangular bar containing a centrally located indexing protuberance 136 to receive and uniquely define the location of a positive pole piece of a battery when located in the battery storage compartment. The drive frame 54 includes ridge aligned with one of the electrically conductive strips for passage into the indexing protuberance 136 to allow electrical connection between pole pieces of the battery and the electrically conductive strips. If desired, the battery may be eliminated and a step down transformer with an AC to DC rectifier can be direct connected to the fan motor.

Figure 21:
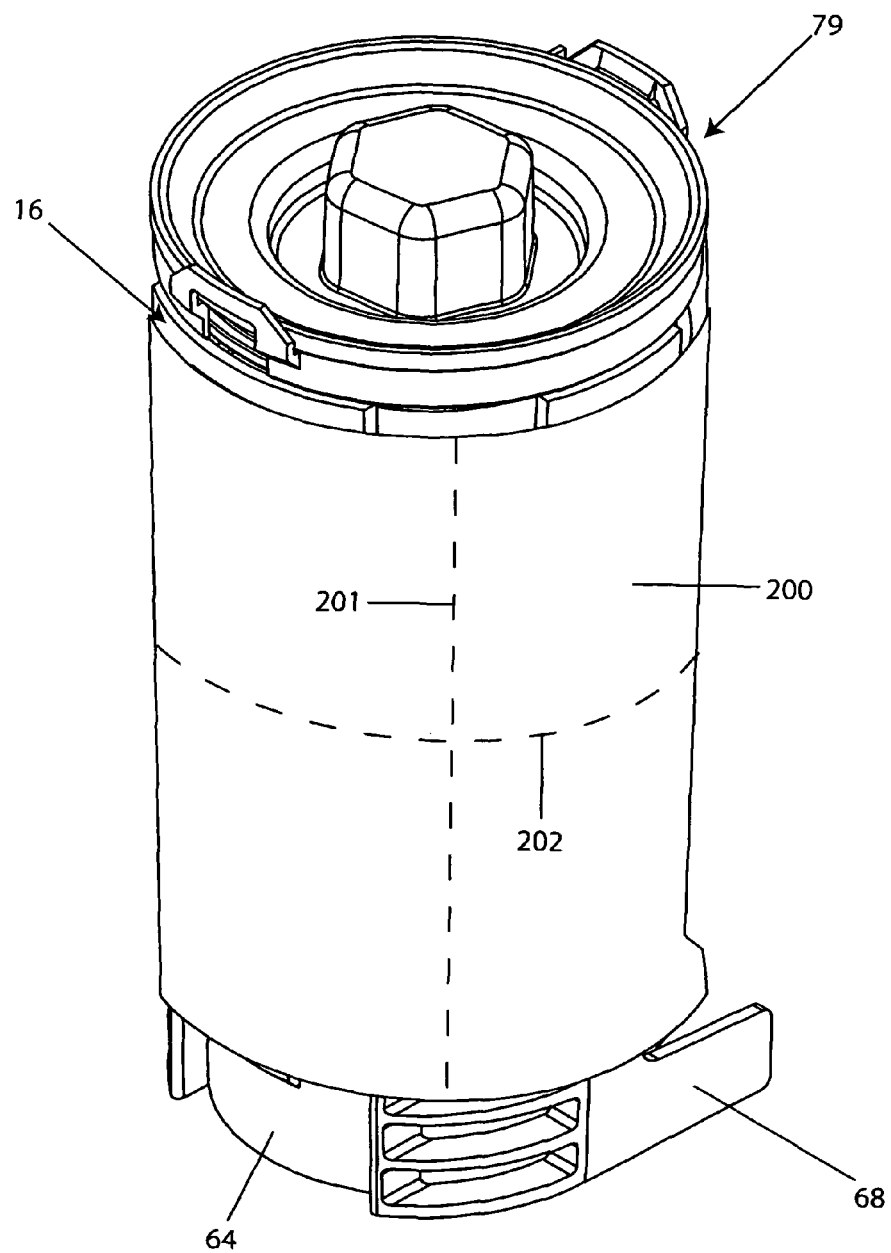
FIG. 21 is an isometric view illustrating the optional feature of a wrapper to control evaporation of the fluid.

As shown in FIG. 21 there is shown the optional feature of providing a wrapper 200 constructed of a sheet of heat shrinkable plastic material fashioned into a tubular shape that can be passed over the vaporizer to substantially completely envelope the outer cylindrical surface. The wrapper 200 stops short to allow exposure of the radically outward extending stabilizer bars 68. The wrapper is formed with diametrically opposed vertical perforations 201 and a perforation 202 encircling the mid portion of the tubular shape. The perforations 201 and 202 are used for controlling the extent to which ambient air can infiltrate the evaporation chamber. More particularly, severing the wrapper 200 along perforation 202 allows removal of an upper half of the wrapper from the ventilating housing 63 of the vaporizer thus avoiding exposure of ambient air to the entire height of the evaporation chamber. The use of the wrapper serves to throttle back the speed of dispensing of the volatile liquid. Severing the wrapper along perforation 201 allows removal of the entire wrapper from the vaporizer thus exposure of ambient air to the entire height of the evaporation chamber and thus serves to maximizing the speed of dispensing of the volatile liquid.

While the present invention has been described in connection with the preferred embodiments of the various figures, it is to be understood that other similar embodiments may be used or modifications and additions may be made to the described embodiment for performing the same function of the present invention without deviating there from. Therefore, the present invention should not be limited to any single embodiment, but rather construed in breadth and scope in accordance with the recitation of the appended claims.

The invention claimed is:

1. An aromatic dispenser apparatus including the combination of:

a dispenser cover including an elongated convexly-shaped central body extended at each side each side having a pair of spaced apart walls and a vent located between said pair of spaced apart walls for ventilating the interior of said dispenser cover, said dispenser cover further including end walls having access openings for ventilating said elongated convexly-shaped central body;

an elongated frame including a receptacle section terminating at a mounting fixture for pivotal support of said dispenser cover between an opened position and an operating position, side guards projecting from said receptacle section to traverse said vent at each side of said of said dispenser cover when in said operating position, said side guards having apertures for ventilating a volume bounded between said side guards and said receptacle section; and a vaporizer including an evaporation chamber supplied with a volatile liquid by a vessel, said vaporizer being fixedly positioned by said mounting fixture to extend between said projecting side guards to infuse air venting from said dispenser cover and side guards with vapors from said evaporation chamber.

2. The aromatic dispenser apparatus according to claim 1 wherein said elongated convexly-shaped central body includes a longitudinal cavity arranged to extend between said end walls for forming a convection guide for airflow to each of said end walls, said spaced apart walls forming boundaries to said longitudinal cavity at each of the opposite lateral sides of said elongated convexly-shaped central body.

3. The aromatic dispenser apparatus according to claim 2 wherein said convection guide comprises circular ring sector shaped walls of said elongated convexly shaped central body.

4. The aromatic dispenser apparatus according to claim 1 further including interconnecting latch bars and apertures carried by said dispenser cover and said elongated frame for inhibiting separation of said dispenser cover from said elongated frame; and a key for releasing said latch bars from said apertures to defeat said inhibiting separation.

5. The aromatic dispenser apparatus according to claim 1 wherein said side guards overlie said evaporation chamber for exposing said vent at each side of said dispenser cover to ventilate vapors from said evaporation chamber.

6. The aromatic dispenser apparatus according to claim 1 wherein said side guards are bounded by spaced sidewall extensions coextensive with said end walls and defining opposed boundary edges of said vents.

7. The aromatic dispenser apparatus according to claim 1 wherein said receptacle section and said vaporizer includes keys and key apertures for proprietary control of the mounting of said vaporizer onto said receptacle section.

8. The aromatic dispenser apparatus according to claim 7 wherein said keys and said key apertures are each dispersed as an array.

9. The aromatic dispenser apparatus according to claim 1 wherein said evaporation chamber has an elongated tubular configuration and said side guards have concave configurations transverse to the extended length of said evaporation chamber to partly wrap in an outwardly spaced relation about said evaporation chamber.

10. The aromatic dispenser apparatus according to claim 1 further including a flange protruding from said vaporizer for suspending said vessel in said evaporation chamber.

11. The aromatic dispenser apparatus according to claim 1 wherein each of said vaporizer and said vessel include confronting truncated conical support surfaces for suspending said vessel in said evaporation chamber.

12. The aromatic dispenser apparatus according to claim 1 wherein said vaporizer further includes a peripheral sidewall integral with a bottom wall forming a reservoir to maintain a supplying said volatile liquid for said evaporation chamber.

13. The aromatic dispenser apparatus according to claim 12 wherein said peripheral sidewall includes parallel and radically outward extending stabilizer bars to engage with said receptacle section when mounting said vaporizer to said elongated frame.

14. The aromatic dispenser apparatus according to claim 13 wherein said upstanding outer peripheral sidewall includes an elongated tubular venting cage extending between said side guards.

15. The aromatic dispenser apparatus according to claim 14 wherein said elongated tubular venting cage includes an array venting windows confronting said elongated convexly shaped central body of said dispenser cover.

16. The aromatic dispenser apparatus according to claim 1 wherein said vaporizer further including a wick in said evaporation chamber for infusion of the volatile liquid from said vessel with the ambient air.

17. The aromatic dispenser apparatus according to claim 16 wherein said evaporation chamber comprises an elongated tubular configuration having resident therein said wick defined with an elongated tubular configuration.

18. The aromatic dispenser apparatus according to claim 1 further including a motor driven fan carried by a drive frame for releasable engagement with said elongated frame for producing an air stream along said elongated convexly-shaped central body of said dispenser cover.

19. The aromatic dispenser apparatus according to claim 18 further including a battery storage compartment comprising opposed end walls confronting pole pieces of a battery when seated against a cylindrical container wall terminating at spaced apart suspension arms for support by said vaporizer.

20. The aromatic dispenser apparatus according to claim 19 further including strips of electrically conductive material extending from said drive frame toward said end walls for contact with pole pieces of a battery when stored in said battery compartment.

21. The aromatic dispenser apparatus according to claim 20 wherein said electrically conductive strips are retained by upstanding arms spaced apart sufficiently to receive said end walls of said battery storage compartment.

22. The aromatic dispenser apparatus according to claim 21 wherein said end walls of said battery storage compartment are arranged to expose pole pieces of a battery while traversing opposite ends thereof.

23. The aromatic dispenser apparatus according to claim 22 wherein said upstanding arms comprise a rectangular bar traversing one end of said battery compartment and a rectangular bar containing a centrally located indexing protuberance to receive and uniquely define the location of a positive pole piece of a battery when located in said battery storage compartment, and wherein drive frame includes ridge aligned with one of said electrically conductive strips for passage into said indexing protuberance to allow electrical connection between pole pieces of said battery and said electrically conductive strips.

* * * * *